United States Patent [19]

Watson

[11] 4,272,344

[45] Jun. 9, 1981

[54] POLYMERIZATION INHIBITOR FOR VINYL AROMATIC COMPOUNDS

[75] Inventor: James M. Watson, Big Spring, Tex.

[73] Assignee: Cosden Technology, Inc., Dallas, Tex.

[21] Appl. No.: 71,379

[22] Filed: Aug. 30, 1979

Related U.S. Application Data

[60] Division of Ser. No. 925,818, Jul. 18, 1978, which is a continuation-in-part of Ser. No. 771,438, Feb. 24, 1977, Pat. No. 4,105,506.

[51] Int. Cl.$^3$ ............... B01D 3/34; C07C 7/05; C07C 7/20
[52] U.S. Cl. ........................ 202/154; 203/9; 203/65; 203/82; 203/84; 203/88; 585/950; 585/806; 585/807
[58] Field of Search ........................ 203/6–9, 203/65, 75, 77, 82, 78, 84, 88, 82; 202/153–155, 158; 585/806, 807, 950

[56] References Cited

U.S. PATENT DOCUMENTS

| | | | |
|---|---|---|---|
| 2,411,264 | 11/1946 | Hachmuth | 203/84 |
| 2,757,130 | 7/1956 | Burns | 203/8 |
| 2,959,626 | 11/1960 | Krausse et al. | 585/430 |
| 3,156,629 | 11/1964 | Ester | 203/82 |
| 3,209,044 | 9/1965 | Meek et al. | 585/805 |
| 3,409,511 | 11/1968 | Rechmeier et al. | 203/78 |
| 3,632,482 | 1/1972 | Hoory et al. | 203/78 |
| 3,844,903 | 10/1974 | Willersinn | 203/84 |
| 4,033,829 | 7/1977 | Higgins | 203/9 |
| 4,191,614 | 3/1980 | Watson et al. | 203/9 |

*Primary Examiner*—Wilbur L. Bascomb, Jr.

[57] ABSTRACT

Disclosed is a process for the distillation of readily polymerizable vinyl aromatic compounds and a new polymerization inhibitor therefor. The process comprises subjecting a vinyl aromatic compound to elevated temperatures in a distillation system in the presence of a new polymerization inhibitor comprising 2,6-dinitro-p-cresol. Also disclosed is a distillation method and apparatus for use with this inhibitor.

5 Claims, 2 Drawing Figures

POLYMERIZATION INHIBITOR FOR VINYL AROMATIC COMPOUNDS

CROSS-REFERENCE TO RELATED APPLICATIONS

The present application is a division of application Ser. No. 925,818, filed on July 18, 1978, which is a continuation-in-part of copending application Ser. No. 771,438, filed Feb. 24, 1977 now U.S. Pat. No. 4,105,506.

BACKGROUND OF THE INVENTION

The present invention relates to a process for the distillation of readily polymerizable vinyl aromatic compounds. More particularly, the present invention relates to a process wherein styrene, substituted styrene, divinylbenzene and polyvinylbenzenes are subjected to elevated temperatures such as in the distillation thereof, wherein the amount of said materials polymerized during distillation is reduced over an extended period of time.

It is well known that vinyl aromatic compounds such as monomeric styrene, lower alkylated styrene, e.g., alpha-methyl styrene, and divinylbenzene polymerize readily, and furthermore, that the rate of polymerization increases with increasing temperature. Inasmuch, as styrene and divinylbenzene produced by common industrial methods contain impurities, these compounds must be subjected to separation and purification processes in order to be suitable for most types of further industrial use. Such separation and purification is generally accomplished by distillation.

In order to prevent polymerization at the conditions necessary to distillation of vinyl aromatic compounds, various types of known polymerization inhibitors have been employed in connection with prior art distillation processes. For example, common inhibitors useful for inhibiting the polymerization of vinyl aromatics under distillation conditions include 4-tert-butylcatechol (TBC) and hydroquinone. It is preferred, however, to purify vinyl aromatics by using vacuum distillation techniques, whereby these commonly employed inhibitors are rendered unsuitable in view of the fact that they are effective only in the presence of oxygen. The partial pressure of oxygen in a vacuum distillation column is accordingly too low for these conventional inhibitors to be effective. Sulphur is perhaps the polymerization inhibitor most commonly employed to inhibit polymerization of vinyl aromatic compounds during distillation, since sulphur does provide effective inhibition in the absence of oxygen. While sulphur provides a reasonably effective inhibitor, its use in distillation processes results in one very significant disadvantage, namely, there is formed in the reboiler bottoms of the distillation column a valueless waste material which is highly contaminated with sulphur. This waste material furthermore represents a significant pollution or waste removal problem, although the disposal problem may be ameliorated somewhat by extracting the sulphur from the distillation bottoms and recycling it back into the distillation system, as described in U.S. Pat. No. 3,629,076. However, this method requires an expensive methanol extraction step.

Although many compounds are effective for inhibiting the polymerization of vinyl aromatic compounds under differing conditions, e.g., storage, other purification techniques, etc., for a number of reasons which are not entirely understood in view of the diverse and unpredictable results obtained, only extremely few of these compounds have proved to be of any utility for inhibiting vinyl aromatic polymerization under distillation conditions, particularly under vacuum distillation conditions. In addition, certain compounds which are useful for inhibiting polymerization of one type of vinyl aromatic compound, for example, styrene, have proved to be essentially ineffective for inhibiting polymerization of another species of vinyl aromatic compound, for example, divinylbenzene. A limited number of nitroso compounds have proven to be effective for inhibiting polymerization of styrene monomer during distillation. For example, N-Nitroso phenylhydroxylamine and p-nitroso-N,N-dimethylaniline are reasonably effective inhibitors for the distillation of styrene, although they are not particularly soluble in styrene monomer. On the other hand, N-Nitroso diphenylamine disclosed in U.S. Pat. No. 3,816,265, assigned to the assignee of the present application has been demonstrated to be a particularly effective polymerization inhibitor under vacuum distillation conditions for both styrene and divinylbenzene, whereas, N-Nitroso-methylaniline as disclosed in U.S. Pat. application Ser. No. 288,138, also assigned to the assignee of the present application, has been found to be an excellent polymerization inhibitor for styrene under vacuum distillation conditions. One of the most effective inhibitor systems known for divinylbenzene comprises a mixture of sulphur and N-Nitroso phenylhydroxylamine. In addition to the nitroid compounds, it has been found that m-nitro-p-cresol is an effective inhibitor. The use of such compound is described and claimed in copending U.S. application No. 749,406, filed Dec. 10, 1976.

In a typical distillation process for vinyl aromatic compounds utilizing a polymerization inhibitor, the mixture of vinyl aromatic to be distilled is generally contacted with the chemical polymerization inhibitor prior to being subjected to distillation conditions in the distillation apparatus. It remains as a significant problem today that the amount of polymer formed in the distillation apparatus and in the high purity product recovered therefrom is substantially higher than desired, and occasionally, that complete polymerization occurs inside of the distillation apparatus. For example, in the process of distilling crude divinylbenzene (a mixture containing divinylbenzenes, diethylbenzenes and monovinylbenzenes) to obtain high purity divinylbenzenes, even when inhibited with sulphur and TBC, a divinylbenzene product is obtained which contains significant quantities of polymer which are difficult to separate from the product and detrimental to the end use of such divinylbenzenes. Furthermore, the material which is removed from the bottom or reboiler area of the distillation apparatus is a highly polluting sulphur-containing waste material which must be disposed of.

It is therefore desirable to provide new polymerization inhibitors which are useful for styrene and vinylbenzenes under elevated temperatures such as those used under distillation conditions, particularly vacuum distillation conditions and which are not subject to the disadvantages outlined above.

SUMMARY OF THE INVENTION

It is therefore an object of the present invention to provide a method for inhibiting the polymerization of readily polymerizable vinyl aromatic compounds during the distillation thereof.

A further object of the invention is to provide a new and improved process for the distillation of readily polymerizable vinyl aromatic compounds, which process results in higher recovery of a high purity unsaturated vinyl aromatic compound and concomitantly in the production of less undesirable by-products.

A further object of the invention resides in the provision of a new and improved process for the distillation of vinyl aromatic compounds which results in the production of substantially less polymerized material in the distillation apparatus.

Yet another object of the invention resides in the provision of a new and improved process for the distillation of vinyl aromatic compounds which avoids the production of a highly polluting, contaminated bottom or reboiler residue.

It is also an object of the present invention to provide a new and improved process for the distillation of vinyl aromatic compounds which permits the distillation apparatus to be operated at an increased rate of throughput without a reduction in efficiency.

It is still a further object of the present invention to provide a new and improved process for the distillation of vinyl aromatic compounds which provides all of the foregoing enumerated advantages in a vacuum distillation process.

A specific object of the present invention resides in the provision of a new and improved polymerization inhibitor system for use at the elevated temperatures required in the distillation of vinyl aromatic compounds.

A further object of the present invention is the provision of a distillation method and apparatus for use with the polymerization inhibitor of the present invention, which maximizes the efficiency thereof.

In accomplishing the foregoing and other objects, there has been provided in accordance with the present invention a process useful for the distillation of a readily polymerizable vinyl aromatic compound comprising subjecting the vinyl aromatic compound to elevated temperatures required as part of the distillation conditions in a distillation system, in the presence of an inhibitor which is 2,6-dinitro-p-cresol.

In one aspect of the process according to the invention, the 2,6-dinitro-p-cresol inhibitor is simply introduced into the distillation system by adding it to the reboiler area of the distillation apparatus, or alternatively, by incorporating it into the incoming stream of vinyl aromatic compound to be purified. The amount of inhibitor necessary to effectively inhibit polymerization of the vinyl aromatic compounds may vary over a wide range depending upon various factors of the distillation process, e.g., temperature, reflux ratio, pressure, residence time, etc. Typically, however, it has been found that an amount of the inhibitor between about 50 and about 3000 ppm is sufficient to inhibit polymerization of vinyl aromatic compounds under normal distillation conditions (105° C. and above).

In another aspect of the present invention, the 2,6-dinitro-p-cresol inhibitor is used in any situation in which the vinyl aromatic compound is subjected to elevated temperatures. For example, should a distillation operation have to be shut down on short notice without time for the vinyl aromatics to be brought back to ambient temperature conditions, then the present invention is particularly useful in preventing the vinyl aromatics within the distillation train from polymerizing.

According to a further embodiment of the instant invention, also provided is a distillation method and apparatus for use with the 2,6-dinitro-p-cresol inhibitor of the present invention. This method comprises introducing a feed of impure vinyl aromatic compound into a distillation apparatus; introducing an effective polymerization inhibiting amount of 2,6-dinitro-p-cresol into the distillation apparatus, and then distilling the feed under distillation conditions of elevated temperature in the presence of the 2,6-dinitro-p-cresol polymerization inhibitor to recover an overhead product of high purity vinyl aromatic product and a residual bottoms fraction having a reduced content of polymeric material. In the preferred embodiment, the vinyl aromatic compound preferably comprises styrene, and is distilled in a distillation train comprising a benzene-toluene column, an ethylbenzene column, and a styrene column, although it is to be emphasized that the distillation method of the present invention is equally advantageous for use with other vinyl aromatic compounds and with other distillation equipment such as would be well known to those skilled in the art.

Moreover, in the preferred embodiment, the 2,6-dinitro-p-cresol is added to the distillation apparatus in the lower or reboiler region thereof or admixed with the styrene feed in order to optimize inhibitor distribution throughout the distillation system, as applicant has found that optimum protection against polymerizaton is achieved when the distribution of inhibitor within each column is commensurate with the distribution of styrene therein. As 2,6-dinitro-p-cresol, hereinafter referred to as DNPC, is volatile, the widest inhibitor protection is obtained by adding the DNPC in this region. In order to conserve inhibitor and thereby reduce operating costs, it is also preferred that at least a portion of the tar produced by the distillation be recycled back to at least the recycle column of the distillation apparatus, as the tar has been found to contain a considerable amount of DNPC which is capable of reuse.

Through the use of the process according to the present invention, the amount of polymerization occurring within the distillation apparatus is significantly reduced in comparison to conventionally employed methods. In addition, the amount of desired distillation product is increased in proportion to the decrease in the amount of polymer formation. Still further, the material accumulating in the bottom or reboiler area of the distillation apparatus can be reused, e.g., for its fuel value or for reprocessing, which is a distinct advantage over conventional methods utilizing sulphur as a polymerization inhibitor which produces a highly polluting waste material in the reboiler area.

Other objects, features and advantages of the present invention will become apparent from the detailed description of the preferred embodiments of the instant invention, taken in conjunction with the Figures of Drawing, wherein:

DESCRIPTION OF THE PREFERRED EMBODIMENTS

Figure 1:
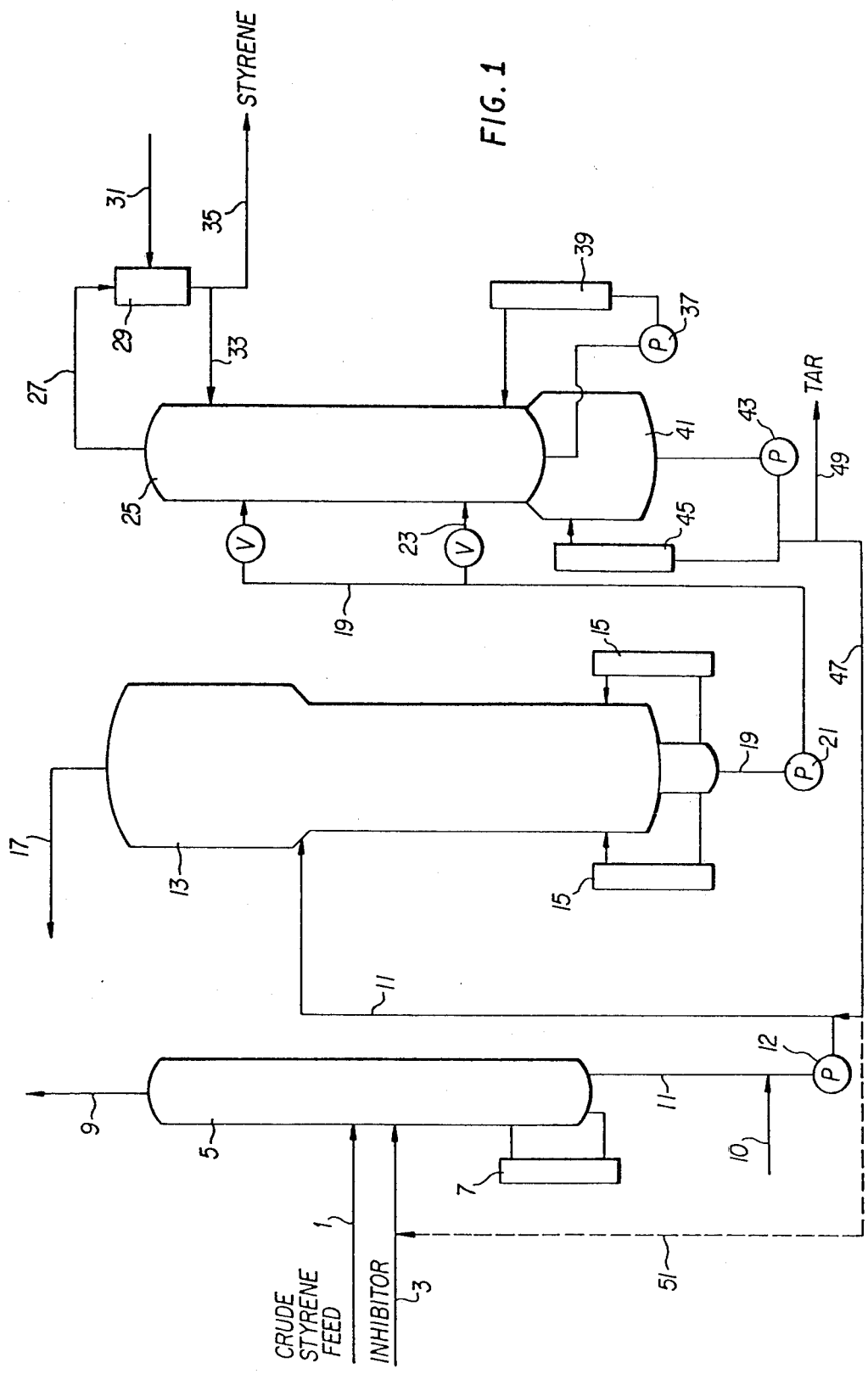
FIG. 1 is a schematic diagram of one embodiment of the distillation method of the present invention applied to a typical three column distillation train comprising a first fractionation column, a recycle column, and a finishing column; and, FIG. 2 is a schematic diagram of the instant distillation method applied to another common distillation train in which a crude vinyl aromatic compound feed is introduced directly into the recycle column wherein the lower boiling components are removed as one overhead fraction and subsequently separated in an off-stream column.

The distillation process of the present invention employs 2,6-dinitro-p-cresol as the polymerization inhibitor during the distillation of vinyl aromatic compounds. Typically, the distillation process is carried out under reduced pressure, e.g., vacuum distillation, and one of the significant advantages of the invention is that the use of sulphur in the distillation system can be avoided.

The distillation techniques of the process of the present invention are suitable for use in virtually any type of separation of a readily polymerizable vinyl aromatic compound from a mixture wherein the vinyl aromatic compound is subjected to temperatures above room temperature. Surprisingly, the process of the present invention has been found particularly useful in vacuum distillation techniques, the preferred method for separating unstable organic liquid mixtures. In its most useful application, the distillation process of the present invention is applied to a distillation mixture containing one of the vinyl aromatic compounds selected from the group consisting of styrene, alpha-methylstyrene, vinyltoluene, vinylnaphthalene, divinylbenzenes and polyvinylbenzenes. The preferred application of the present invention relates to the distillation of crude divinylbenzene or crude styrene under vacuum distillation conditions.

The amount of polymerization inhibitor added may vary over a wide range depending upon the conditions of distillation. Generally, the degree of stabilization is proportional to the amount of inhibitor added. In accordance with the present invention, it has been found that inhibitor concentrations generally between about 50 ppm and about 3000 ppm by weight have generally provided suitable results, depending primarily upon the temperature of the distillation mixture and the degree of inhibition desired. More often, however, with the inhibitor of the present invention it is used in concentrations of 100 to 1000 ppm.

During vacuum distillation of the divinylbenzene-containing mixtures and styrene-containing mixtures, the temperature of the reboiler is preferably maintained from about 150° F. to about 250° F. by controlling reboiler pressure at from about 30 mm to about 400 mm of Hg. Under such conditions, in a distillation apparatus having a distillation zone containing from about 50 to about 100 distillation stages, inhibitor mixture concentrations of from about 100 ppm to about 2000 ppm by weight are suitable, whereas concentrations of from about 100 ppm to about 600 ppm by weight are preferably, 200 to 600 ppm by weight, in the case of styrene distillation and concentrations in the range of from about 200 ppm to about 1000 ppm by weight are preferred for distillation of divinylbenzene. The foregoing ranges are based upon distillation temperatures of from 150° to 250° F. and residence times of between about 2 and 4 hours. Obviously, in the lower portions of the temperature and residence time ranges, smaller amounts of inhibitor may be utilized. Obviously, amounts of inhibitor greater than those specified hereinabove may be employed, although the advantages of adding the additional inhibitor are not significant and are outweighed by the corresponding increase in cost.

The polymerization inhibitor of the present invention may be introduced into the distillation apparatus in any convenient manner which permits efficient distribution of the inhibitor throughout the apparatus. Typically and most advantageously, the required amount of inhibitor is simply added to the reboiler area of the distillation column, although equivalent results may be obtained by incorporating the inhibitor into the incoming hot stream of vinyl aromatic compound. Also, the inhibitor may be added at both reboiler and directly into the distillation column. Either and/or both methods of addition provide a distribution of inhibitor which is commensurate with the distribution of the vinyl aromatic compound within the distillation system and is essential for effective polymerization inhibition.

Since the inhibitor is gradually depleted during distillation, it is generally necessary to maintain the appropriate amount of inhibitor in the distillation apparatus by adding inhibitor during the course of the distillation process. Such addition may be carried out either on a generally continuous basis or it may consist of intermittent charging of inhibitor into the distillation system. The means by which the maintenance of the necessary concentration of the inhibitor system is carried out is of no particular importance as long as the concentration of inhibitor is kept about the minimum required level.

One method by which the amount of inhibitor which is gradually depleted during distillation and the increased cost necessitated thereby may be minimized is by recycling a portion of the distillation residue or tar back into the distillation system. Applicant has found that the distillation residue contains a substantial quantity of DNPC polymerization inhibitor which may be reutilized in the distillation system with a concomitant reduction in the process requirements for additional inhibitor. Moreover, by recycling a portion of the tar, the amount of DNPC inhibitor within the distillation system may be significantly increased, thereby enhancing protection against polymerization within the system.

The tar may be recycled back into the distillation system at any desirable point therein such as would be obvious to those skilled in the art. However, in a typical distillation train comprising a first fractionation column, a recycle column, and a finishing column, adequate inhibitor protection within the recycle column has been found to be essential to the elimination of thermal polymer, since the high distillation temperatures necessary to achieve adequate fractionation between the similar boiling compounds separated therein causes the formation of a substantial portion of the total thermal polymer formed within the distillation system as a whole. Indeed, with conventional processes, approximately 80% of the total thermal polymer formed is attributable to the recycle column. Accordingly, in the preferred embodiment, the portion of tar recycled is recycled to at least the recycle column, and preferably into the lower regions of the recycle column in order to provide a locus of DNPC distribution which corresponds to the distribution of vinyl aromatic compound therein. Optionally, additional tar may be recycled for addition back into the distillation system at other points, such as, for example, back into the first fractionation column.

One convenient method by which the tar may be recycled back into the distillation system is simply by incorporating the tar into an incoming feed of vinyl aromatic compound or DNPC inhibitor. The amount of tar which is recycled back into the distillation system relative to the amount of feed may comprise any desirable amount. A larger amount of tar recycle will increase the loading of DNPC within the distillation system. However, larger amounts of tar recycle will also increase the volume of bottoms material, and the amount of tar recycle will necessarily be constrained thereby.

Referring to the drawings, FIG. 1 illustrates the application of the distillation method of the present invention to a conventional styrene distillation train comprising a benzene-toluene fractionation column 5, referred to in the industry as a B-T column, an ethylbenzene or recycle column 13, and a styrene or finishing column 25, although it is to be emphasized that the operational principles of the instant distillation method are highly suitable for use, with minor modification, with the distillation equipment utilized in the purification of other vinyl aromatic compounds. As shown in FIG. 1, a heated crude styrene feed is introduced into the intermediate portion of B-T column 5 through feed line 1. The B-T column 5 may be of any suitable design known to those skilled in the art and may contain any suitable number of vapor-liquid contacting devices, such as bubble cap trays, perforated trays, valve trays, etc. Usually, however column 5 contains less than 40 distillation trays. Column 5 is also equipped with a suitable reboiler 7 for supplying heat thereto.

While most of the thermal polymer is formed in the ethylbenzene or recycle column 13, a small but significant amount of the total thermal polymer formed during distillation is formed in the B-T column 5. Accordingly, a polymerization inhibitor is essential within this column. To this end, the DNPC polymerization inhibitor may be introduced into the B-T column 5 as a separate stream through line 3, or it may be incorporated into the crude styrene feed flowing through line 1 for introduction into this column. When the DNPC polymerization inhibitor is added to the B-T column 5 as a separate stream, the DNPC is preferably dissolved in a volatile aromatic hydrocarbon diluent. The volatile aromatic hydrocarbon diluent may comprise any suitable volatile aromatic hydrocarbon in which the DNPC inhibitor is soluble. By way of example, this diluent may include benzene, toluene, ethylbenzene, or styrene itself. Preferably, however, the volatile aromatic diluent comprises styrene since use of this diluent permits the distribution of the DNPC inhibitor to correspond with the locus of distribution of styrene within the column. Generally, effective polymerization inhibition can be achieved by providing an inhibitor distribution which is coincident with the distribution of the readily polymerizable vinyl aromatic compound.

Under the distillation conditions imposed in column 5, an overhead stream comprising benzene and toluene is removed from the column via line 9. These low-boiling aromatic hydrocarbons are subsequently condensed and passed to storage for further use. The bottoms product in the B-T column, comprising styrene, ethylbenzene, inhibitor, and tar, serves as charge to the recycle or ethylbenzene column 13 and is introduced into the intermediate portion thereof by means of line 11 and pump 12. In order to reduce the viscosity of the B-T column bottoms product, a non-volatile hydrocarbon diluent may be introduced into line 11 and thence into recycle column 13 by way of line 10. Any suitable non-volatile hydrocarbon diluent may be used, the only requirements being that the non-volatile diluent is stable and sufficiently higher boiling than styrene for ready separation by fractionation. Typical materials used for this purpose include isopropylbenzene, butylbenzene, and xylene bottoms. Preferably, however, the non-volatile hydrocarbon diluent comprises a polyethylbenzene residue. The ethylbenzene or recycle column 13 may be of any suitable design known to those skilled in the art and may contain from 40 to 100 trays. Preferably, however, the recycle column is of the parallel path design, i.e., two parallel distillation paths descending through the column. Additionally, it is also preferable that the recycle column contain a large number of trays, i.e., 72 in order to achieve a proper separation between the similar boiling styrene and ethylbenzene. The B-T bottoms are preferably introduced into the intermediate portion of the recycle column 13. Inhibitor protection within the ethylbenzene column 13 is provided by the DNPC which is present in the B-T bottoms which are charged thereto. Additionally, the loading of inhibitor within this column is preferably supplemented by the recycle of tar thereto, as will be explained more fully hereinafter. Each side of the distillation column 13 also has connected therewith a reboiler 15.

The ethylbenzene overhead product of the recycle column 13 is withdrawn through line 17 and is subsequently condensed for reuse in an ethylbenzene dehydrogenation reactor. The recycle bottoms, comprising styrene, inhibitor, polyethylbenzene diluent if utilized, and tar is withdrawn from the reboiler area of the recycle column 13 through line 19. The recycle bottoms is then fed by pump 21 into the intermediate portion of the styrene or finishing column 25 through line 19. Optionally, the bottoms material may also be introduced into the lower portion of the styrene column 25 through line 23.

The finishing column 25 may be of any suitable design known to those skilled in the art. A typical column will contain, for example, about 24 distillation trays. A reboiler 39, preferably a forced flow reboiler, is also connected thereto in order to supply heat to the column. Due to the high viscosity of the styrene column bottoms, pump 37 is also preferably employed to circulate the bottoms through reboiler 39 and into styrene column 25. Generally, inhibitor protection is adequately provided in this column by the DNPC inhibitor present in the feed. Since, however, inhibitor is gradually removed from the distillation system, in order to insure adequate inhibitor protection throughout the distillation train, the DNPC inhibitor is preferably continuously added to the system through line 3, or in admixture with the crude styrene feed through line 1, and a portion of the tar is recycled at least back into the ethylbenzene column 13 in order to further supplement the amount of DPNC within the system. Conventionally, moreover, tertiary-butylcatechol (TBC) is admixed with the high purity styrene overhead product in reflux accumulator 29, through line 31, and a portion of this mixture is returned to the styrene column 25 as reflux through line 33, providing thereby further protection against polymerization.

The high purity styrene overhead product withdrawn through line 27 from the styrene column 25 will generally be above 97% and even above 99% by weight styrene, depending upon the ultimate use. As has been mentioned, the high purity styrene overhead product is admixed with a polymerization inhibitor which is suitable to prevent polymerization during storage, conventionally TBC, in reflux accumulator 29. The majority of the purified styrene is withdrawn through line 35 to storage to await its ultimate use. The styrene column bottoms product is composed of polystyrene, undistilled styrene, polyethylbenzene, and the DPNC inhibitor. This fraction is withdrawn from the styrene column 25 into flash pot 41 for further processing as indicated by arrow 40. The flash pot 41 is shown as comprising a bottom section of the styrene column 25. However, it should be obvious to those skilled in the art that a separate unit could also be used. In the flash pot 41, residual styrene is removed from the bottoms from the styrene column and recycled back thereto as indicated by arrow 42. A reboiler 45 supplies heat to the bottoms product in flash pot 41, which is circulated by pump 43. The tar produced in the flash pot 41 is withdrawn from the system on a continuous basis through line 49.

In one particularly preferred embodiment of the present invention, a portion of the tar, containing substantial amounts of the DNPC inhibitor, is recycled through line 47 for introduction into the ethylbenzene column 13. The portion of tar which is recycled may be added to the ethylbenzene column 13 by any method known to those skilled in the art. Best results are obtained, as has been discussed supra, by adding the tar at a location in the ethylbenzene column which will give a distribution of DNPC inhibitor which coincides with the distribution of styrene therein. Conveniently, this may be done by incorporating the recycled tar into the incoming feed for the ethylbenzene column 13, which flows through line 11. Optionally, additional DNPC-containing tar may be recycled for introduction into the distillation train at other points, such as, for example, the B-T column 5 via line 51. By recycling the DNPC-containing tar, the DNPC inhibitor may thus be reused, accruing thereby a significant reduction in the process requirements for inhibitor. Moreover, tar recycle enables the inhibitor loading to be conveniently increased within the distillation train, particularly within the critical ethylbenzene column which has been shown to contribute approximately 80% of the total thermal polymer formed during distillation.

Figure 2:
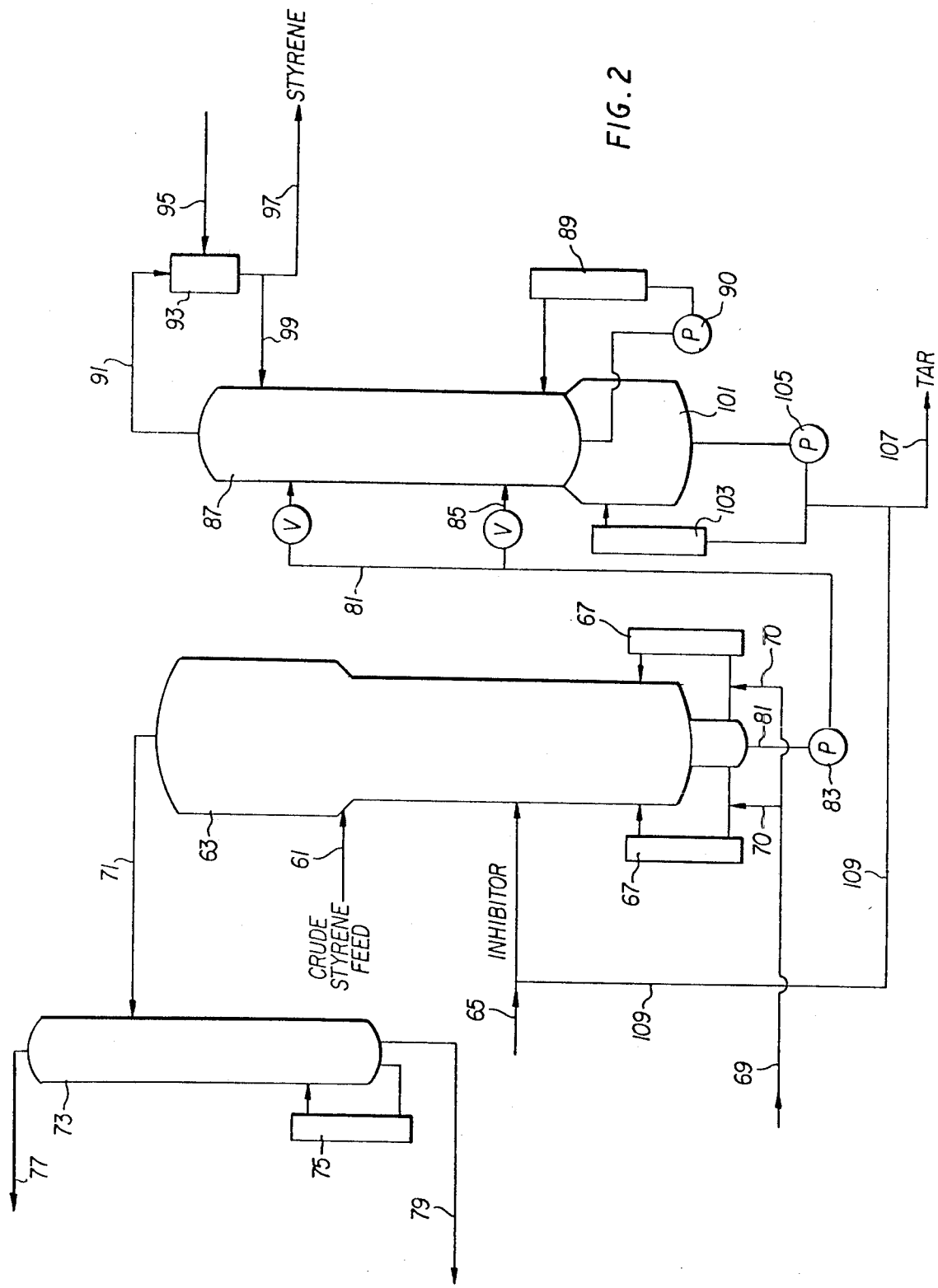

FIG. 2 illustrates the application of the distillation method of the present invention to another typical distillation train for styrene. A styrene feed is introduced into the intermediate portion of recycle column 63, which is preferably of the parallel distillation path design. Line 65 supplies the DNPC inhibitor to the recycle column 63, preferably in the form of a DNPC-volatile hydrocarbon diluent solution. Heat is supplied to the bottoms of the column 63 by means of reboilers 67. Preferably, a polyethylbenzene residue diluent is introduced into the reboilers 67 through line 69 and divergent legs 70.

An overhead product comprising benzene, toluene, and ethylbenzene is withdrawn through line 71 for subsequent fractionation in distillation column 73. In column 73, benzene and toluene are withdrawn as an overhead fraction and are subsequently condensed for further use. An ethylbenzene bottoms product is withdrawn through line 79, and is recycled for use in an ethylbenzene dehydrogenation reactor. Reboiler 75 provides the B-T column 73 with the necessary heat for distillation. Since no polymerizable vinyl aromatic material is present in the B-T column 54, the presence of an inhibitor therein is unnecessary.

The recycle bottoms product, comprising polystyrene, undistilled styrene, polyethylbenzene, and DNPC inhibitor is withdrawn from recycle column 63 through line 81. The impure styrene fraction is then charged to the upper portion of the styrene column 87 by means of pump 83. Optionally, impure styrene may be introduced into the lower region of the styrene column 87 through line 85. A reboiler circuit comprising reboiler 89 and pump 90 is attached to the styrene or finishing column 87 for supplying the necessary heat thereto. The purified styrene overhead product is withdrawn through line 91 to the reflux accumulator 93, wherein it is mixed with TBC arriving via line 95. A portion of this product is recycled through line 99 for addition to the finishing column 87 as reflux. The major portion of the purified styrene is withdrawn through line 97 to storage.

The finishing column bottoms product is directed to flash pot 101 for further processing as indicated by arrow 100. The flow of vapors from the flash pot back to the finishing column is indicated by arrow 102. Flash pot 101 has connected thereto a suitable reboiler circuit comprising reboiler 103 and pump 105 to facilitate the further fractionation of the bottoms. The tar produced during the distillation process is withdrawn through line 107. In the preferred embodiment, a portion of this tar is recycled to the recycle column 63 through line 109 in order to conserve inhibitor and to supplement the inhibitor loadings within that column.

Use of the distillation method of the present invention thus enables a distillation apparatus to operate with an increased rate as opposed to conventional prior art processes since the distribution and loading of DNPC inhibitor is optimized within the distillation train. By optimizing the distribution of the DNPC inhibitor within the recycle column to correspond with the locus of distribution of the vinyl aromatic compound, the amount of thermal polymer formed is substantially reduced over that occurring in conventional distillation processes. Consequently, higher distillation temperatures and higher pressures may be utilized without the formation of objectionable amounts of thermal polymer. In this manner, the rate of distillation may be increased without increasing the amount of polymerization which has been deemed to be acceptable in accordance with conventional distillation procedures.

Another factor enabling the distillation apparatus to operate at an increased rate in accordance with the present invention as opposed to conventional prior art processes is the fact that the inhibitor system of the present invention is a more efficient inhibitor at normal temperatures than the conventional inhibitors, and will thus permit higher distillation temperatures and higher pressures. In this way, the rate of distillation can be increased without increasing the amount of polymerization which has been deemed to be acceptable in accordance with conventional distillation procedures.

When the process of the present invention is utilized, the bottoms material which accumulates during the distillation process can be drawn off and utilized for its heating value or for reprocessing. This represents another significant advantage in comparison to conventional processes for vacuum distillation of vinyl aromatic compounds which employ sulphur as the polymerization inhibitor, or sulphur in combination with other chemical polymerization inhibitors. In these conventional processes, a bottoms material is formed which is valueless for further use and constitutes a high polluting waste material which must be disposed of and which, in this regard, also presents a problem of disposal.

Upon recovery of the distillation product obtained from the process of the present invention, it is found that a higher percentage of the pure readily polymerizable vinyl aromatic compound is recovered in an unpolymerized state. Moreover, the concentrated distillation residues have a lower viscosity than those produced by conventional processes and are more easily handled and removed from the apparatus, as by pumping or the like.

In order to more fully describe the present invention, the following examples are presented which are intended to be merely illustrative and not in any sense limitative of the present invention.

EXAMPLE 1

50 grams of styrene free of tert-butyl catechol were placed in a 100 ml. flask fitted with a stirrer. The flask was also fitted with a reflux condenser open to the air. There was then added to the flask 400 ppm of 2,6-dinitro-p-cresol. The flask and contents were heated in an oil bath which is thermostatically controlled at 115° C. ±2° C. 1 ml. samples of the styrene are periodically withdrawn from the flask and are mixed with 3 ml. of methanol to determine the qualitative extent of polymerization. At the end of five hours, there was still no significant precipitation of styrene polymer indicating m-nitro-p-cresol to be an effective retardant to polymerization during distillation of styrene.

EXAMPLE 2

Example 1 is repeated substituting divinylbenzene for styrene. Substantially equivalent results are obtained.

While the invention has now been described in terms of certain preferred embodiments, and exemplified with respect thereto, the skilled artisan will readily appreciate that various modifications, changes, omissions, and substitutions may be made without departing from the spirit thereof. Accordingly, it is intended that the present invention be limited solely by the scope of the following claims.

What is claimed is:

1. Apparatus for the distillation of a readily polymerizable vinyl aromatic compound employing as a polymerization inhibitor 2,6-dinitro-p-cresol, comprising:
    a. a first fractionation column having reboiler means connected thereto for maintaining the bottoms of said column at a proper temperature, feed lines for introducing a vinyl aromatic compound into said column, and product lines for recovering an overhead product and a bottoms fraction therefrom;
    b. means for introducing said polymerization inhibitor into the bottoms of said first fractionation column;
    c. a second fractionation column having reboiler means connected thereto, a feed line for transporting the bottoms of said first column to said second column for further distillation, and a product line for recovering an overhead product and a bottoms fraction;
    d. a third fractionation column having reboiler means connected thereto, a feed line for transporting the bottoms of said second column to said third column for further distillation, and a product line for recovering an overhead product of high purity vinyl aromatic compound and a bottoms fraction;
    e. a flash stripper connected to said third fractionation column for vaporizing residual vinyl aromatic compound from the bottoms fraction of said third column and recycling the vaporized vinyl aromatic compound from said bottoms of said third column back to said third column; and
    f. means for recycling a portion of the bottoms of said flash stripper back to said second column.

2. The apparatus of claim 1, further comprising means for recycling another portion of the bottoms of said flash stripper back to said first fractionation column.

3. The apparatus of claim 1, further comprising a reflux accumulator connected to the product line of said third column for collecting said purified vinyl aromatic compound and returning a portion thereof to said third column as reflux.

4. Apparatus for the distillation of a readily polymerizable vinyl aromatic compound employing 2,6-dinitro-p-cresol as a polymerization inhibitor therein, comprising:
    a. a first fractionation column having reboiler means connected thereto for maintaining the bottoms of said column at a proper temperature, feed lines for introducing a vinyl aromatic compound into said column, and product lines for recovering an overhead product and a bottoms fraction therefrom;
    b. means for introducing said polymerization inhibitor into the bottoms of said first column;
    c. a second fractionation column which receives the overhead product from said first column for further distillation, said second column having reboiler means connected thereto, and product lines for recovering overhead and bottoms streams therefrom;
    d. a third fractionation column having reboiler means connected thereto, a feed line for transporting the bottoms of said first column to said third column for further distillation, and a product line for recovering an overhead product of high purity vinyl aromatic compound and a bottoms fraction;
    e. a flash stripper connected to said third fractionation column for vaporizing residual vinyl aromatic compound from the bottoms fraction of said third column and recycling the vaporized vinyl aromatic compound from said bottoms of said third column back to said third column; and
    f. means for recycling a portion of the bottoms of said flash stripper back to said first column.

5. The apparatus of claim 4, further comprising a reflux accumulator connected to the product line of said third column for collecting said purified vinyl aromatic compound and returning a portion thereof to said third column as reflux.

* * * * *